(12) United States Patent
Paranjape et al.

(10) Patent No.: US 12,295,729 B2
(45) Date of Patent: May 13, 2025

(54) APPARATUS AND METHOD FOR DELIVERY OF ANTIMICROBIAL DURING A TRANSDERMAL SAMPLING AND DELIVERY PROCESS

(71) Applicant: Georgetown University, Washington, DC (US)

(72) Inventors: Makarand Paranjape, Silver Spring, MD (US); Shruti M. Paranjape, Silver Spring, MD (US)

(73) Assignee: Georgetown University, Washington, DC (US)

( * ) Notice: Subject to any disclaimer, the term of this patent is extended or adjusted under 35 U.S.C. 154(b) by 464 days.

(21) Appl. No.: 17/553,286

(22) Filed: Dec. 16, 2021

(65) Prior Publication Data

US 2022/0104732 A1    Apr. 7, 2022

Related U.S. Application Data

(62) Division of application No. 15/226,475, filed on Aug. 2, 2016, now Pat. No. 11,219,390.

(Continued)

(51) Int. Cl.
*A61B 5/145*     (2006.01)
*A61B 5/1477*    (2006.01)
(Continued)

(52) U.S. Cl.
CPC ........ *A61B 5/14514* (2013.01); *A61B 5/1477* (2013.01); *A61B 5/150076* (2013.01);
(Continued)

(58) Field of Classification Search
CPC .............. A61B 5/14532; A61B 5/1486; A61B 5/14514; A61B 5/6833; A61B 2562/04; A61B 5/14521; A61B 5/1491

See application file for complete search history.

(56) References Cited

U.S. PATENT DOCUMENTS

4,526,176 A    7/1985   Bremer et al.
4,708,716 A    11/1987  Sibalis
(Continued)

FOREIGN PATENT DOCUMENTS

EP    0 942 278       9/1999
JP    H01-158343      6/1989
(Continued)

OTHER PUBLICATIONS

Using electrospun poly(ethylene-oxide) nanofibers for improved retention and efficacy of bacteriolytic antibiotics; John W. Gatti, Marie C. Smithgall, Shruti M. Paranjape, Ronda J. Rolfes, Makarand Paranjape; Biomedical Microdevices, Oct. 2013, vol. 15, Issue 5, pp. 887-893 (Year: 2013).*

(Continued)

*Primary Examiner* — Thaddeus B Cox
*Assistant Examiner* — Karen E Toth
(74) *Attorney, Agent, or Firm* — Dawn-Marie Bey; Bey & Cotropia PLLC

(57) ABSTRACT

A device for introducing at least one antimicrobial in an exposed region of a user's skin caused while accessing interstitial fluid includes a substrate having thereon at least one electrically controllable microheating element including at least a microheater portion with multiple electrodes connected to the microheater portion for forming a micropore in the user's skin. A nanofiber mat loaded with at least one antimicrobial material is arranged on the substrate such that it contacts the user's skin and encircles an opening of the micropore formed by the microheating element. In a preferred embodiment, the at least one antimicrobial material is LL-37.

8 Claims, 6 Drawing Sheets

Related U.S. Application Data

(60) Provisional application No. 62/200,421, filed on Aug. 3, 2015.

(51) Int. Cl.
*A61B 5/15* (2006.01)
*A61B 5/157* (2006.01)
*A61B 18/14* (2006.01)

(52) U.S. Cl.
CPC .. *A61B 5/150328* (2013.01); *A61B 5/150969* (2013.01); *A61B 5/157* (2013.01); *A61B 18/14* (2013.01)

(56) References Cited

U.S. PATENT DOCUMENTS

| | | | |
|---|---|---|---|
| 4,775,361 | A | 10/1988 | Jacques et al. |
| 4,821,733 | A | 4/1989 | Peck |
| 4,909,256 | A | 3/1990 | Peck |
| 5,123,902 | A | 6/1992 | Muller et al. |
| 5,176,881 | A | 1/1993 | Sepaniak et al. |
| 5,203,327 | A | 4/1993 | Schoendorfer et al. |
| 5,330,527 | A | 7/1994 | Montecalvo et al. |
| 5,362,307 | A | 11/1994 | Guy et al. |
| 5,380,272 | A | 1/1995 | Gross |
| 5,422,246 | A | 6/1995 | Koopal et al. |
| 5,591,139 | A | 1/1997 | Lin et al. |
| 5,722,397 | A | 3/1998 | Eppstein |
| 5,730,714 | A | 3/1998 | Guy et al. |
| 5,801,057 | A | 9/1998 | Smart et al. |
| 5,885,211 | A | 3/1999 | Eppstein et al. |
| 6,056,738 | A | 5/2000 | Marchitto et al. |
| 6,124,597 | A | 9/2000 | Shehada et al. |
| 6,233,471 | B1 | 5/2001 | Berner et al. |
| 6,312,393 | B1 | 11/2001 | Abreu |
| 6,393,318 | B1 | 5/2002 | Conn et al. |
| 6,464,687 | B1 | 10/2002 | Ishikawa et al. |
| 6,730,212 | B1 | 5/2004 | Yamagishi et al. |
| 6,887,202 | B2 | 5/2005 | Currie et al. |
| 7,344,499 | B1 | 3/2008 | Prausnitz et al. |
| 7,655,477 | B1 | 2/2010 | Schneider et al. |
| 7,888,509 | B2 | 2/2011 | Wolf et al. |
| 7,931,592 | B2 | 4/2011 | Currie et al. |
| 8,568,315 | B2 | 10/2013 | Currie et al. |
| 8,929,968 | B2 | 1/2015 | Brister et al. |
| 9,332,937 | B2 | 5/2016 | Currie et al. |
| 2003/0225362 | A1 | 12/2003 | Currie et al. |
| 2005/0182307 | A1* | 8/2005 | Currie ............... A61M 5/1723 600/300 |
| 2006/0115857 | A1 | 6/2006 | Keen |
| 2006/0200232 | A1* | 9/2006 | Phaneuf ............. D04H 1/43838 623/1.42 |
| 2006/0204738 | A1* | 9/2006 | Dubrow ................. A61F 13/02 428/292.1 |
| 2007/0027383 | A1 | 2/2007 | Peyser et al. |
| 2009/0308742 | A1 | 12/2009 | Paranjape |
| 2010/0018641 | A1* | 1/2010 | Branham ............. D01D 5/0038 264/466 |
| 2010/0021552 | A1* | 1/2010 | Hayes .................... A61L 15/46 424/618 |
| 2010/0028504 | A1 | 2/2010 | Perry |
| 2010/0285084 | A1* | 11/2010 | Yang ...................... A61L 27/54 424/94.4 |
| 2011/0042225 | A1 | 2/2011 | Adeloju |
| 2011/0111012 | A1* | 5/2011 | Pepper ............... A61F 13/00995 156/60 |
| 2011/0229551 | A1* | 9/2011 | Doshi .................... D01D 5/0007 514/180 |
| 2012/0010487 | A1 | 1/2012 | Currie et al. |
| 2012/0060589 | A1 | 3/2012 | Gridelet et al. |
| 2012/0150004 | A1 | 6/2012 | Currie et al. |
| 2013/0041235 | A1 | 2/2013 | Rogers et al. |
| 2013/0150763 | A1* | 6/2013 | Mirzaei .............. A61F 13/0206 264/413 |
| 2014/0004159 | A1* | 1/2014 | Xie ..................... A61L 27/3633 424/572 |
| 2014/0025000 | A1 | 1/2014 | Currie et al. |
| 2015/0072008 | A1* | 3/2015 | Tornero Garcia ....... A61K 9/70 604/289 |
| 2016/0025626 | A1* | 1/2016 | Dos Santos Fegadolli ................ G01N 21/0332 422/82.05 |

FOREIGN PATENT DOCUMENTS

| | | |
|---|---|---|
| JP | H05-172815 | 7/1993 |
| JP | H07-000541 | 1/1995 |
| JP | H09-140687 | 6/1997 |
| WO | WO 97/42882 | 11/1997 |
| WO | WO 99/44507 | 9/1999 |
| WO | WO 99/58050 | 11/1999 |
| WO | WO 00/04832 | 2/2000 |
| WO | WO 00/15102 | 3/2000 |
| WO | WO 00/018289 | 4/2000 |
| WO | WO 09/025698 | 2/2009 |
| WO | WO 2014/149161 | 9/2014 |
| WO | WO2014/149514 | * 9/2014 ............... A61B 5/05 |

OTHER PUBLICATIONS

"Poly Lactic-co-Glycolic Acid (PLGA) as Biodegradable Controlled Drug Delivery Carrier", Hirenkumar K. Makadia and Steven J. Siegel, Polymers (Basel). Sep. 1, 2011; 3(3): 1377-1397 (Year: 2011).*
U.S. Appl. No. 13/835,696, Paranjape.
U.S. Appl. No. 13/459,392, Paranjape, et al.
U.S. Appl. No. 13/384,199, Paranjape.
Abdelrahman M. Abdelgawad, Samuel M. Hudson, Orlando J. Rojas, "Antimicrobial Wound Dressing Nanofiber Mats From Multicomponent (Chitosan/Silver-NPs/Polyvinyl Alcolol) Systems," Carbohydrate Polymers, http://dx.doi.org/10.1016/j.carbpol.2012.12.043 (2013) 13 pp.
Bingyun, Li, et al., "Evaluation of Local MCP-1 and IL-12 Nanocoatings for Infection Prevention in Open Fractures," Journal or Orthopaedic Research, 7 pp., Jan. 2020.
Noore, Jabeen, et al., "Cationic Antimicrobial Peptide LL-37 Is Effective Against Both Extra- and Intracellular *Staphylococcus aureus*," Antimicrobial Agents and Chemotherapy, vol. 57, No. 3, pp. 1283-1290, Mar. 2013.
International Search Report and Written Opinion for Application No. PCT/US16/45162, dated Oct. 21, 2016, 8 pp.
Li, et al., "Multilayer Polypeptide Nanoscale Coatings Incorporating IL-12 for the Prevention of Biomedical Device-Associated Infections," Biomaterials, vol. 30, Issue 13, pp. 2552-2558, May 2009.
Li, et al., "Evaluation of Local MCP-1 and IL-12 Nanocoatings for Infection Prevention in Open Fractures," J. Orthop. Res. 28(1):48-54, Jan. 2010.
J. W. Gatti, et al., "Using Electrospun Poly(ethylene-Oxide) Nanofibers for Improved Retention and Efficacy of Bacteriolytic Antibiotics," Biomed. Microdevices, vol. 15, Issue 5, pp. 887-893 (7 pp.), Oct. 2013.
"Bio-Functionalized Nanofibers," Pan-American Advanced Studies Institute (PASI), 7 pp., Aug. 4-12, 2011.
J. W. Gatti, "Using Electrospun Poly(Ethylene-Glycol) Nanofibers for Localized Delivery of Antibiotics," Senior Thesis, 44 pp.
Ball, et al., "Drug-Eluting Fibers for HIV-1 Inhibition and Contraception," PLOS One, vol. 7, Issue 11, 14 pp., Nov. 2012.
Vandamme, et al., "A Comprehensive Summary of LL-37, the Factotum Human Cathelicidin Peptide," Cellular Immunology 280, pp. 22-35, 2012.
Song, et al., "Multi-Biofunction of Antimicrobial Peptide-Immobilized Silk Fibroin Nanofiber Membrane: Implications for Wound Healing," Acta Biomater., vol. 39, pp. 146-155, Jul. 15, 2016.
Patent Examination Report No. 1 for Application No. AU 2013201044, dated Jan. 20, 2014, 4 pp.

(56) References Cited

OTHER PUBLICATIONS

International Search Report and Written Opinion for Application No. PCT/US14/19183. dated May 14, 2014, 7 pp.

Preliminary Examination Report for Application No. PCT/US01/17081, dated Sep. 15, 2004 (mailing date).

International Search Report for App. No. PCT/US01/17081.

Using electrospun poly(ethylene-oxide) nanofibers for improved retention and efficacy of bacteriolytic antibiotics; John W. Gatti, Marie C. Smithgall, Shruti M. Paranjape, Ronda J. Rolfes, Makarand Paranjape; Biomedical Microdevices, Oct. 2013, vol. 15, Issue 5, pp. 887-893.

"SpectRX An Innovative Medical Technology Company" [online], Copyright 2004 [retrieved on Aug. 31, 2004], 1 p., Retrieved from the Internet: http://www.spectrx.com.

Written Opinion for Application No. PCT/US01/17081, dated Feb. 13, 2004 (mailing date).

Schneider, T., et al., "B-Fit uSystem: Bio-Flips Integrable Transdermal MicroSystem," ARO Workshop on Biomolecular Signaling, Energy, Transfer, and Transduction Processes, Cashiers, NC, May 14-17, 2000, 16 pp.

Smith, Frederick P. and Kidwell, David A., "Cocaine in Hair, Saliva, Skin Swabs, and Urine of Cocaine Users' Children," Forensic Science Intl., vol. 83, pp. 179-189, 1996.

Balabanova, Vol Svetla and Schneider, E., "Detection of Drugs in Sweat (Nachweis von Drogen im Schweiß)," Beitr. Gerichtl. Med., vol. 48, pp. 45-49, 1990.

Peck, Carl C., et al., "Outward Transcutaneous Chemical Migration: Implications for Diagnostics and Dosimetry," Skin Pharmacol., vol. 1, No. 1, pp. 14-23, 1988.

Supplementary European Search Report for Application No. EP 01 93 9501, dated Jan. 11, 2011.

Phillips, Michael and McAloon, Margaret H., "A Sweat-Patch Test for Alcohol Consumption: Evaluation in Continuous and Episodic Drinkers," Alcohol: Clinical and Experimental Research, vol. 4, No. 4, pp. 391-395, 1980.

Henderson, Gary L. and Wilson, B. Kent, "Excretion of Methadone and Metabolites in Human Sweat," Research Communications in Chemical Pathology and Pharmacology, vol. 5, No. 1, pp. 1-8, Jan. 1973.

Paranjape, et al., "A PDMS Dermal Patch for Non-Intrusive Transdermal Glucose Sensing," Sens. Actuat. A, 2003, vol. 104, pp. 195-204 (2003), Entire Document.

Connolly, et al., "Minimally Invasive Sensing," Ch. 18 of "Biosensors—Emerging Materials and Applications," Jul. 2011, ISBN: 978-953-307-328-6, pp. 355-382 (Jul. 2011), entire documents [online], download from: http://cdn.intechweb.org/pdfs/16435.pdf> on Mar. 30, 2013.

PCT Communication for Application No. PCT/US2013/27126, filed Feb. 21, 2013, "Notification of the International Search Report and Written Opinion of the International Searching Authority, or the Declaration," Apr. 26, 2013.

Zhang, et al., J. Matl. Sci. Matls. In Medicine 16 (2005), pp. 933-946.

Martinez, et al., PNAS 105(5), 19606-19611 (2008).

Martinez, et al., Anal. Chem., 82:3-10 (2010).

Abe, et al., Analyt. Chem. 80 (2008) (6928-6934).

Li, et al., Analyt. Chem. 80 (2008) (9131-9134).

Chronakis, et al., Polymer 47(5): 1597-1603 (2006).

Miao, et al., J. Nanosci. Nanotech. 10:5507-5519 (2010).

Shiroma, et al., Analytica Chimica Acta 725 (2012) (44-50).

Dungchai, et al., Analyt. Chem. 81 (2009) (5821-5826).

Liu, et al., Matl. Sci. Eng. C27(1):57-60 (Jan. 2007).

Yamada, et al., Chem. Lett. 26(3):201-202 (1997).

Fortier, et al., Biosens. Bioelectronics 5:473-490 (1990).

Paranjape, Makarand, "Pain-Free Diabetic Monitoring Using Transdermal Patches," SPIE Newsroom, 2008, 2 pp.

International Search Report and Written Opinion for Application No. PCT/US14/11296, pp., dated Feb. 25, 2015.

Kastantin, Mark J., et al., "Integrated Fabrication of Polymeric Devices for Biological Applications," Sensors and Materials, vol. 15, No. 6, pp. 295-311, 2003.

Gadre, A. P., et al., "Fabrication of a Fluid Encapsulated Dermal Patch Using Multilayered SU-8," Sensors and Actuators A 114, pp. 478-485, 2004.

* cited by examiner

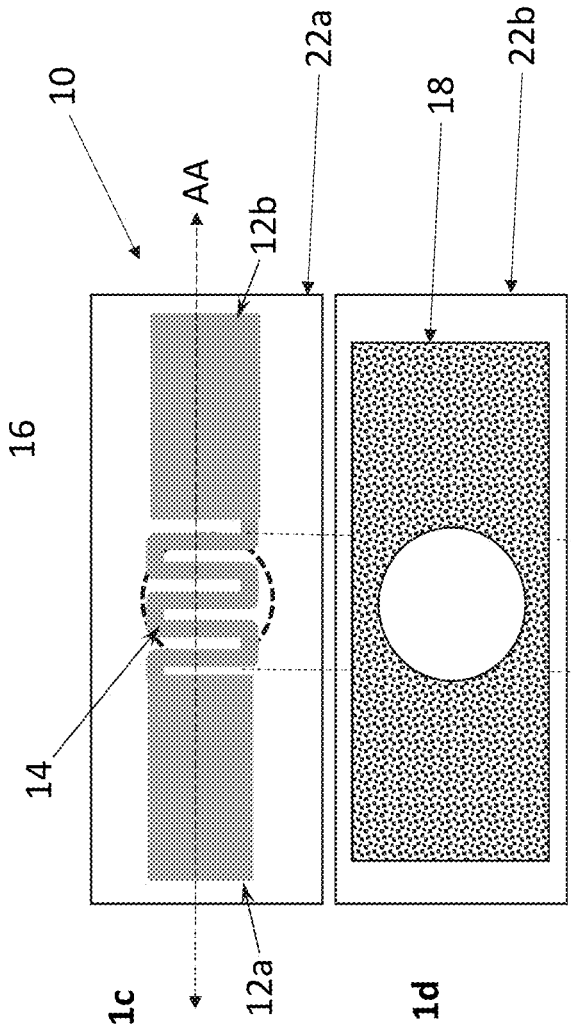
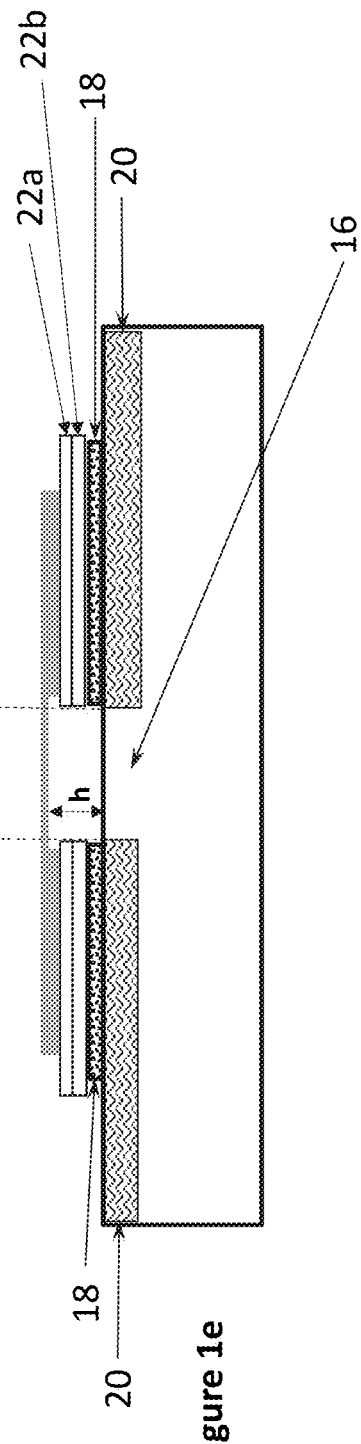
Figure 1c
Figure 1d
Figure 1e

APPARATUS AND METHOD FOR DELIVERY OF ANTIMICROBIAL DURING A TRANSDERMAL SAMPLING AND DELIVERY PROCESS

CROSS-REFERENCE TO RELATED APPLICATIONS

The present application is a division of U.S. application Ser. No. 15/226,475, filed Aug. 2, 2016, titled "Apparatus and Method For Delivery of Antimicrobial During a Transdermal Sampling and Delivery Process," which claims priority to and the benefit of similarly titled U.S. Provisional Patent Application No. 62/200,421, filed Aug. 3, 2015, both of which are incorporated herein by reference in their entireties.

BACKGROUND

Medical sampling, monitoring and drug delivery systems and processes continue to evolve with a focus on minimization of invasiveness to the patient. By way of example, the following co-owned patents and patent applications are directed to various transdermal sampling and delivery technologies and are incorporated herein by reference in their entireties: U.S. Pat. Nos. 6,887,202, 7,931,592, 8,568,315 and USP application Ser. No. 14/036,966 directed to Systems and Methods for Monitoring Health and Delivering Drugs Transdermally; USP application Ser. No. 13/459,392 directed to Electrochemical Transdermal Glucose Measurement System Including Microheaters and Process For Forming; USP application Ser. No. 13/835,696 directed to Microfluidic Systems For Electrochemical Transdermal Glucose Sensing Using a Paper-Based or Other Wicking Substrate; and USP application Ser. No. 13/384,199 directed to Microfluidic Systems for Electrochemical Transdermal Analyte Sensing Using a Capillary-Located Electrode (collectively, "Patent Documents").

While the primary goal of these transdermal systems is to provide minimally invasive devices and processes for collecting and analyzing samples, e.g., blood, interstitial fluid, for analytes and/or for providing medications responsive thereto (e.g., transdermal drug delivery), even a minimally invasive system can leave the access location vulnerable to various microorganisms or microbes, e.g., bacteria, fungi, viruses, which may reside on the user's skin and/or on the devices. Such microorganisms can migrate into the body through the access location, e.g., micropore, causing a potential adverse (negative) response. Some of these microorganisms include drug-resistant bacteria, also called superbugs (e.g., MRSA, C-*difficile*) which are increasingly resistant to known antibiotics.

Prior research has been conducted in the related area of preventing and/or treating in vivo bacterial infections at open wound sites, such as open fracture sites, using nanocoatings on orthopedic implants. See, Li et al., Multilayer polypeptide nanoscale coatings incorporating IL-12 for the prevention of biomedical device-associated infections, Biomaterials, Volume 30, Issue 13, May 2009, Pages 2552-2558 and Li et al., Evaluation of local MCP-1 and IL-12 nanocoatings for infection prevention in open fractures. J. Orthop. Res. 28:48-54. But far less invasive devices and procedures can also increase user susceptibility to microorganisms.

Accordingly, there is a need in the art for an apparatus and process for mitigating possible negative secondary effects resulting from the use of minimally invasive medical sampling, monitoring and drug delivery devices.

Additionally, the risk of infection at surgical and other wound sites dressed with sutures and/or other closure materials remains an issue, particularly with the rise of antibiotic resistant super bugs in the hospital or other medical treatment settings. Accordingly, an on-going need exists for the mitigation of this infection risk.

In addition to the patents and patent applications listed above, the following documents are incorporated herein by reference in their entireties and are intended to provide examples of the skill in the art and supporting description for one or more aspects of the embodiments described and illustrated herein: J. W. Gatti et al., Using electrospun poly(ethylene-oxide) nanofibers for improved retention and efficacy of bacteriolytic antibiotics, Biomed Microdevices, October 2013, Volume 15, Issue 5, pp 887-893; Bio-Functionalized Nanofibers, Pan-American Advanced Studies Institute (PASI), Aug. 4-12, 2011; J. W. Gatti, Using Electrospun Poly(ethylene-glycol) Nanofibers for Localized Delivery of Antibiotics, Senior Thesis; Ball et al., Drug-Eluting Fibers for HIV-1 Inhibition and Contraception, PLOS One, Vol. 7, Issue 11, November 2012; Vandamme et al., "A comprehensive summary of LL-37, the factotum human cathelicidin peptide," Cellular Immunology 280, pgs. 22-35 (2012); and Song et al., "Multi-biofunction of antimicrobial peptide-immobilized silk fibroin nanofiber membrane: Implications for wound healing," Acta Biomater. Volume 39, 15 Jul. 2016, Pages 146-155.

SUMMARY OF THE EMBODIMENTS

In a first exemplary embodiment, a device for introducing at least one antimicrobial in an exposed region of a user's skin caused while accessing interstitial fluid of a user includes a substrate having thereon a mechanism for accessing the interstitial fluid of the user; and a nanofiber mat loaded with at least one antimicrobial material.

In a second exemplary embodiment, a hand-held device for electrochemically monitoring an analyte in interstitial fluid of a user includes: a first end configured to contact the skin of the user, the first end including a mechanism for ablating the skin of the user to form a micropore to access interstitial fluid and further including a nanofiber mat formed thereon, the nanofiber mat including at least one antimicrobial material; a cartridge connected to the first end and having disposed therein a plurality of disposable sensing elements for contacting interstitial fluid from the micropore to monitor an analyte therein; and a second end connected electrically and mechanically to the cartridge and the first end for facilitating operation of the mechanism for ablating the skin, dispensing of a disposable sensing element and monitoring of the analyte.

In a third exemplary embodiment, a patch having multiple individually controllable sites for accessing interstitial fluid of a user and monitoring at least one analyte therein, includes a substrate having formed thereon the multiple individually controllable sites each including: a mechanism for producing a micropore in the user's skin and accessing the interstitial fluid of the user and a nanofiber mat loaded with at least one antimicrobial material; and an adhesive for adhering the patch to the skin of the user.

BRIEF SUMMARY OF THE FIGURES

The Summary of the Embodiments, as well as the following Detailed Description, is best understood when read in conjunction with the following exemplary drawings:

FIGS. 1c-1e show a second representative heating element with antimicrobial mat configuration in accordance with an embodiment herein;

DETAILED DESCRIPTION

Figures 1A, 1B:
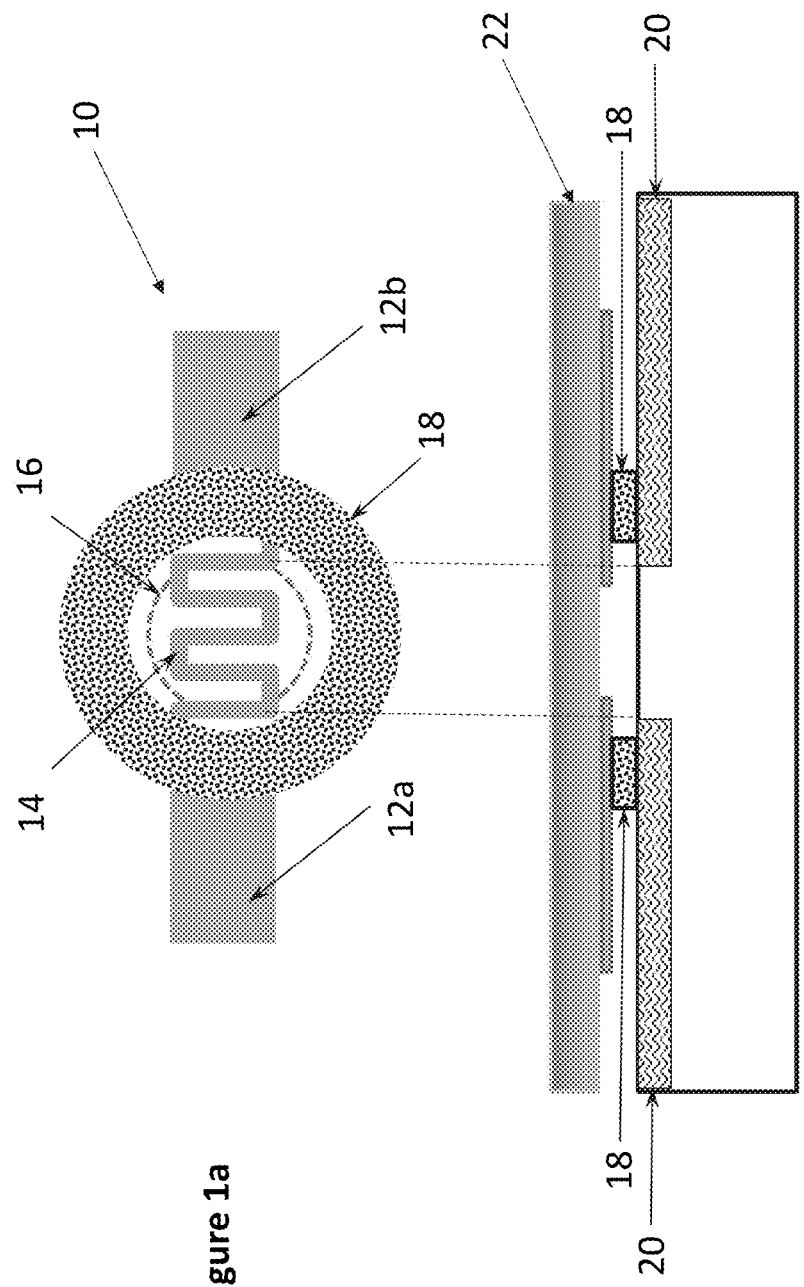
FIGS. 1a and 1b show a first representative heating element with antimicrobial mat configuration in accordance with an embodiment herein.

FIGS. 1a and 1b illustrate a singular microheating element 10 which includes resistive heater electrodes 12a, 12b which are connected by a microheater portion 14 for generating a localized thermal pulse when an appropriate voltage is applied thereto. The resistive heater electrodes 12a, 12b form a closed circuit and upon application of an appropriate voltage for an approximate length of time thereto, act to ablate a portion of the stratum corneum 20 of the individual, creating a micropore 16 therein on the order of microns in diameter. Such ablation, though minimally invasive, makes the individual more susceptible at the site of the micropore 16 to various microorganisms or microbes, e.g., bacteria, fungi, viruses, which may reside on the user's skin or on a portion of the contacting instrument. Accordingly, the microheating element 10 further includes an annulus-shaped nanofiber mat 18 which has been loaded with an antimicrobial, such as, for example LL-37. The width of the annulus being on the order of approximately 5-25 The microheating element 10 is formed on a substrate 22.

The applied voltage specifications, i.e., volts/time, may vary in accordance with patient age and size. For example, devices used on adult human patients may be configured to apply 3V (with respect to ground) for, e.g., 30 msec, resulting in a rapid ablation of a portion of the patient's stratum corneum creating an approximately 50 μm diameter micropore therein. Whereas, the same or a different device, may be configured for use with premature human patients where the stratum corneum has minimal thickness. In this case, one skilled in the art recognizes that the applied voltage, time and resulting pore diameter would be reduced.

Further, while the specific representative embodiments described and illustrated herein include the nanofiber mat 18 as being part of the microheating element 10, one skilled in the relevant art understands that variations which provide for the nanofiber mat 18 being in close proximity to the resulting micropore 16, but not necessarily on the microheating element 10, fall well within the scope of the present embodiments. For example, referring to FIGS. 1c-1e, a different configuration and ordering of elements includes microheating element 10 having resistive heater electrodes 12a, 12b which are connected by a microheater portion 14 formed on a first substrate 22a having a hole therethrough at the point adjacent the microheater portion 14. FIG. 1d shows a second substrate 22b including an antimicrobial nanofiber mat (or layer) 18 thereon, with a hole therethough having a diameter slightly larger than the hole in the first substrate 22a. And in FIG. 1e, the first and second substrates are aligned back-to-back with the holes aligned to form the final transdermal device. The gap height h from the microheater portion 14 and the skin, i.e., stratum corneum 20 is small, such that the heat from the microheater portion 14 is sufficient to cause the desired ablation and form micropore 16.

Additional details regarding the formulation, layout, dimensions and operation of the microheating element 10 are described in the co-owned patents and patent applications (collectively, "Patent Documents") listed in the Background section above. Multiple microheating elements 10 may be used in an array as discussed in the Patent Documents, wherein multiple individual microheating elements 10 each having a nanofiber mat 18 on or associated therein are included in an array. The array may be included on a substrate, e.g., patch, wherein each of the individual microheating elements 10 is individually controllable/usable, thus resulting in multiple micropores over the course of time and use of the array.

Figure 2:
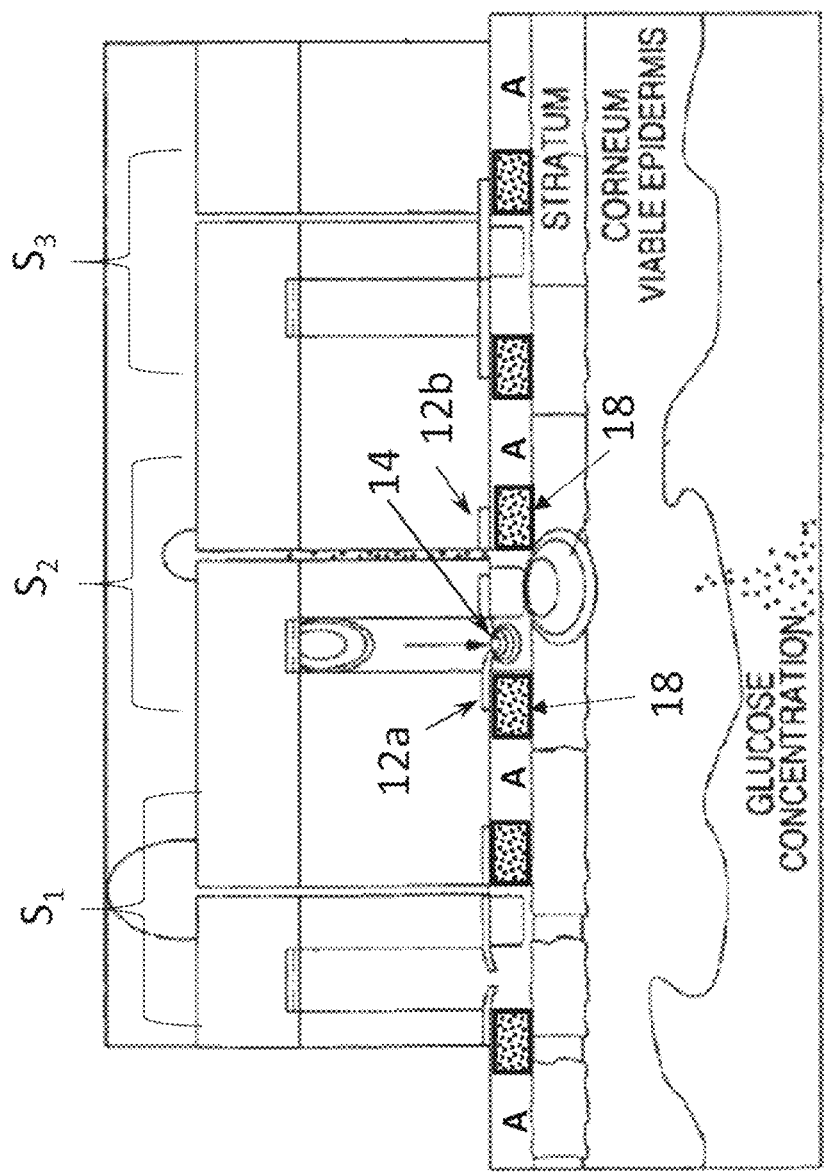
FIG. 2 shows a particular multiple use device having a heating element with antimicrobial mat configuration in accordance with an embodiment herein.
Figure 3:
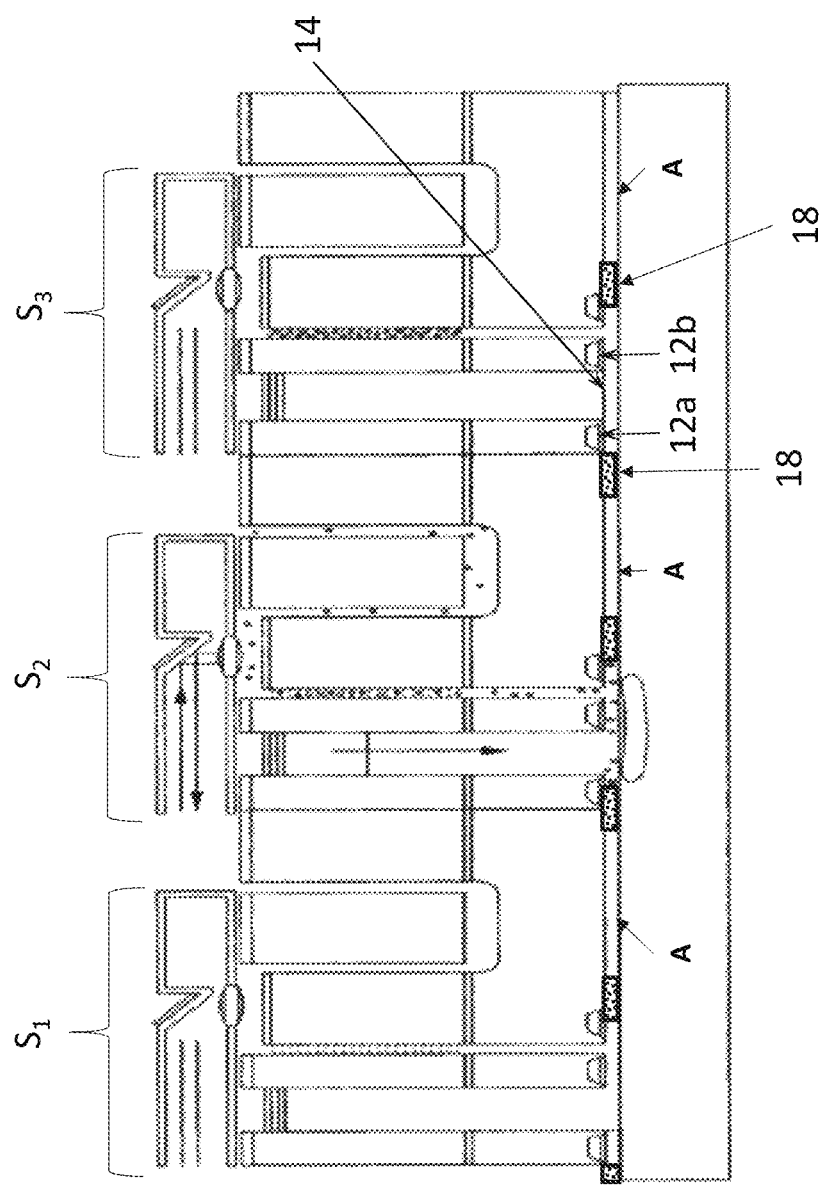
FIG. 3 shows a particular multiple use device having a heating element with antimicrobial mat configuration in accordance with an embodiment herein.

FIGS. 2 and 3 illustrate portions of exemplary multiple use devices, which include multiple individually controllable sites ($S_1, S_2, S_3 \ldots S_x$), each site including components similar to those illustrated in FIGS. 1a and 1b or equivalents thereof. Use of each of $S_1, S_2, S_3 \ldots S_x$ results in a micropore which, as discussed previously, makes the individual more susceptible at the site of the micropore to various microorganisms or microbes, e.g., bacteria, fungi, viruses, which may reside on the user's skin or on a portion of the contacting instrument. Accordingly, as illustrated, individual nanofiber mats 18 are incorporated at each site ($S_1, S_2, S_3 \ldots S_x$) adjacent to the micropore and in contact with the user's skin. Alternating with the nanofiber mats is adhesive A for adhering the multiple use device to the skin of the user.

FIGS. 2 and 3 illustrate particular devices wherein the microheater portion 14 acts to both create the micropore and to release a physiological compatible solution, e.g., saline, from a reservoir in the device which mixes with interstitial fluid released from micropore and travels up a detection path in the device to a detector (not shown, but described in one or more Patent Documents). The device provides for "on-demand" analysis and the inclusion of the nanofiber mat 18 with antimicrobial provides added protection to the user at the spent sites, e.g., $S_1$. A physiological solution is preferably expelled onto the exposed viable epidermis and recovered into the transport capillary. One skilled in the art recognizes that the micro-heater and the physiological solution seal may be the same or different; the heater and seal may, therefore, be electrically connected either in series or parallel. Additionally, the physiological compatible solution may or may not contain one or more drugs.

Alternatively, the device may be a single-use device. Whether the microheating element is part of a single-use device or a multi-use device, the effectiveness of the nanofiber mat 18 or more specifically, the antimicrobial, may be enhanced by keeping the device in place for a predetermined amount of time, e.g., at least 2 hours, or an approximate amount of time calculated for the micropore 16 in the stratum corneum to begin closing up.

A description of exemplary processes for formation of the nanofiber mat for use in the embodiment described herein may be found in one or more of the documents listed in the section Documents Incorporated by Reference. The immobilization of antimicrobial peptides and peptide motifs on nanofiber membranes has been achieved and the effectiveness of the antimicrobial nanofiber membranes as both an antibiotic and a wound healing facilitation material has been determined. In a specific exemplary embodiment, the nanofiber mat 18 may be formed using electrospinning techniques to generate nanofibers having varying diameters, e.g., 100-500 nm, from a solution of poly(ethylene-oxide) (PEO) and the antimicrobial peptide, LL-37 as discussed in detail in J. W. Gatti et al., Using electrospun poly(ethylene-oxide) nanofibers for improved retention and efficacy of bacteriolytic antibiotics, Biomed Microdevices, October 2013, Volume 15, Issue 5, pp 887-893.

The antimicrobial LL-37 is selected as the exemplar microbial herein for its broad bacteria killing ability. More specifically, LL-37 has been shown to kill the following bacteria as discussed in Vandamme et al., "A comprehensive summary of LL-37, the factotum human cathelicidin peptide," Cellular Immunology 280, pgs. 22-35 (2012): *Bacillus anthracis; Enterococcus faecalis*; Group A *streptococcus*; Group B *Streptococcus; Lactobacillus casei; Listeria monocytogenes; Micrococcus luteus; Nocardia* sp.; *Propionibacterium acnes; Staphylococcus aureus; Streptococcus mutans; Streptococcus pneumonia; Borrelia* spp.; *Mycobacterium bovis; Mycobacterium smegmatis; Mycobacterium tuberculosis; Achromobacter xylosoxidans; Acinetobacter baumannii; Aggregatibacter actinomycetemcomitans; Brucella suis; Burkholderia pseudomallei; Burkholderia cepacia; Burkholderia thailandensis; Capnocytophaga* spp.; *Escherichia coli; Francisella novicida; Fusobacterium nucleatum; Haemophilus influenza; Helicobacter pylori; Klebsiella pneumonia; Leptospira interrogans; Mannheimia haemolytica; Pasteurella multocida; Porphyromonas circumdentaria; Porphyromonas gingivalis; Prevotella intermedia; Prevotella loescheii; Prevotella melaninogenica; Pseudomonas aeruginosa; Salmonella* sp.; *Shigella* sp.; *Stenotrophomonas maltophilia; Tannerella forsythia; Treponema denticola; Treponema pallidum* and *Yersinia pestis*.

Figure 4A:
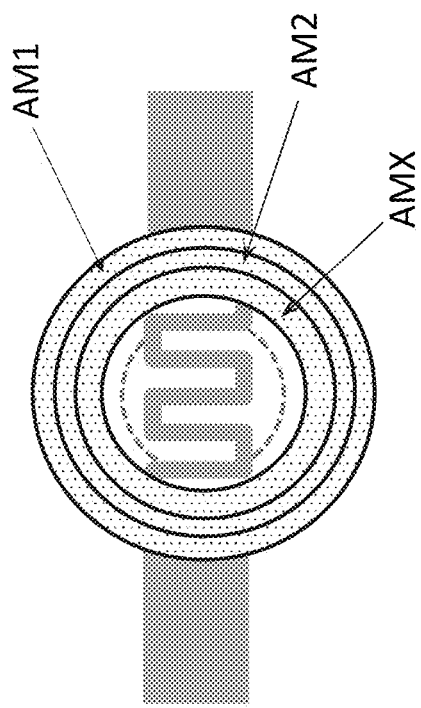
FIGS. 4a and 4b show a representative heating element with alternative antimicrobial mat configurations in accordance with an embodiment herein wherein multiple antimicrobial materials are incorporated in to the same mat.
Figure 4B:
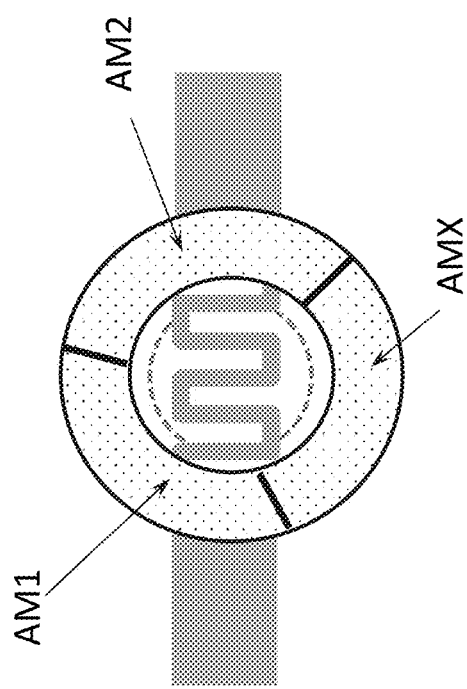

One skilled in the art readily recognizes that other antimicrobials may be used, either alone, or in combination with LL-37 to cover a wider range of bacteria. FIGS. 4a-4b illustrate an annulus-shaped nanofiber mat which includes multiple antimicrobials (AM1, AM2, . . . AMX) loaded therein.

Figure 5B:
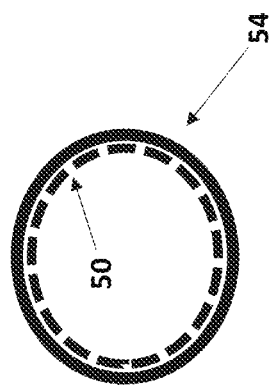
FIGS. 5a-5c show an exemplary hand-held device incorporating a microheater in conjunction with an antimicrobial mat.
Figure 5C:
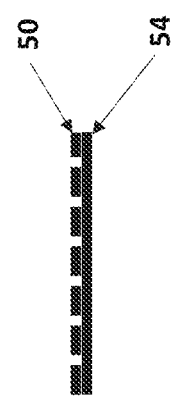
Figure 5A:
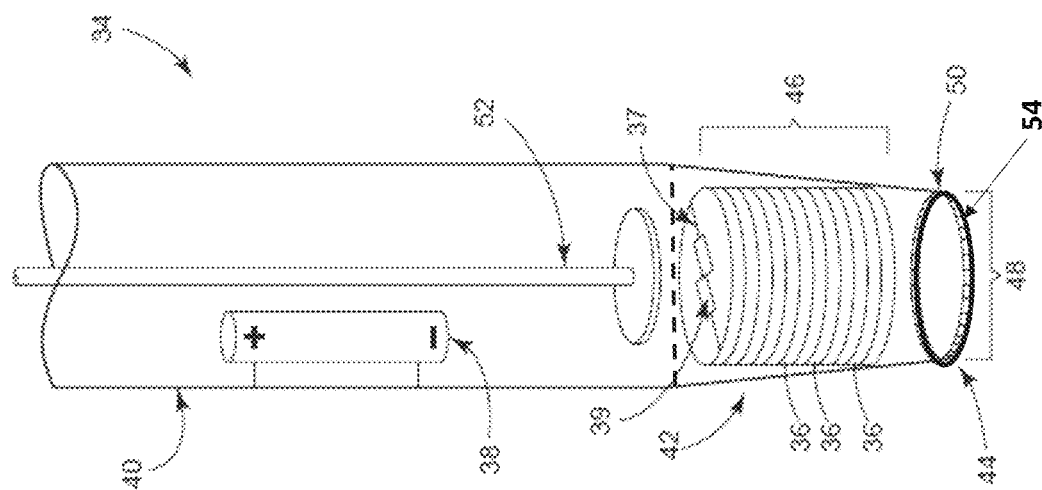

The incorporation of an antimicrobial is also contemplated with respect to, e.g., a hand-held device for electrochemically monitoring an analyte in interstitial fluid of a user, such as that disclosed in co-owned U.S. patent application Ser. No. 13/835,696. Components of an exemplary device 34 are illustrated in FIGS. 5a-5c. The device includes a plurality of sensing elements 36, each comprising a system of electrodes, as described above, on an individual portion of a paper-based or other wicking substrate. Each individual sensing element has a system of conductive elements 37 connectable to a controllable voltage source 38 within the device, and each comprises at least one electrode 39 modified with a sensing material, such as glucose oxidase (GOx), for measuring the level of the analyte in a fluid which contacts the sensing element.

Although not shown, connective elements located e.g. in the inner wall of device 34 can serve to place elements 37, 39, and/or 50 (as described below) in contact with the controllable voltage source 38.

With further reference to FIGS. 5a-5c, the device preferably includes a handle region 40 attached to an end region 42 having an open tip 44. (In practice, the tip could be a closed tip which is openable prior to use.) In a specific embodiment of the hand-held device, the end region 42 may be single-use cartridge that may be discarded and replaced as needed. The end region includes a storage region 46, for containing a predetermined number of sensing elements 36, adjacent the open tip. The periphery 48 of the open tip comprises a conductive microheater element 50, which is connectable to the voltage source 38 within the device, and a ring of antimicrobial mat 54 deposited thereon. The antimicrobial mat 54 may of sufficient thickness, e.g. nanometers to millimeter, to last through the use of all of the predetermined number of sensing elements 36 in the cartridge, i.e., end region 42. The location of the antimicrobial mat 54 may be adjacent to the outer rim of the microheater element 50 as shown in FIG. 3b or in a stacked configuration as shown in FIG. 5c, so long as the antimicrobial mat 54 is contacting the skin of the user. Additional details regarding configurations and operation of the hand-held device are described in U.S. patent application Ser. No. 13/835,696 which is incorporated herein by reference in its entirety.

While the particular examples above are directed to certain exemplary transdermal devices, one skilled in the art appreciates that the antimicrobial nanofiber mat or coating may be incorporated into other medical equipment that invades the body, including, but not limited to syringes, catheters, etc.

As referenced briefly in the Background, the risk of infection at surgical and other wound sites dressed with sutures and/or other closure materials is an on-going concern. The antimicrobial nanofiber materials referenced above may form or be incorporated into various dressings including, but not limited to biodegradable fibrous mesh, biodegradable suture (e.g., a polymer) or non-biodegradable suture (e.g., silk nanofibers) containing LL-37 or other antimicrobial. As with the nanofiber mats described herein, these dressings form a barrier to foreign bodies.

The invention claimed is:

1. A device for introducing at least one antimicrobial in an exposed region of a user's skin caused while accessing interstitial fluid of a user comprising:
    a substrate having thereon multiple individually controllable sites for accessing interstitial fluid of a user, each of the multiple individually controllable sites including:
        a mechanism for accessing the interstitial fluid of the user having at least one electrically controllable microheating element including at least a microheater portion with multiple electrodes connected to the microheater portion configured to cause a micropore in the user's skin by thermal ablation of at least a portion of the skin's stratum corneum; and
        a generally ring shaped nanofiber mat loaded with multiple antimicrobial materials including LL-37, wherein the nanofiber mat has a ring width of 5 to 25 µm and is disposed directly on at least a portion of the microheating element on a skin-facing side of the substrate and arranged on the at least a portion of the microheating element such that it is configured to contact the user's skin and encircle an opening of the micropore.

2. The device of claim 1, wherein the multiple antimicrobial materials are located in different portions of the generally ring shaped nanofiber mat.

3. The device of claim 2, wherein the different portions are individual sub-rings comprising the generally ring shaped mat.

4. The device of claim 2, wherein the different portions are alternating radial sections of the generally ring shaped nanofiber mat.

5. A patch including multiple individually controllable sites for accessing interstitial fluid of a user and monitoring at least one analyte therein, comprising:
 a substrate having formed thereon the multiple individually controllable sites each including:
  a mechanism configured to produce a micropore in the user's skin and configured to access the interstitial fluid of the user the mechanism having at least one electrically controllable microheating element including at least a microheater portion with multiple electrodes connected to the microheater portion configured to produce the micropore in the user's skin by thermal ablation of at least a portion of the skin's stratum corneum; and
  a generally ring shaped nanofiber mat loaded with multiple antimicrobial materials including LL-37, wherein the nanofiber mat has a ring width of 5 to 25 µm and is disposed directly on at least a portion of the microheating element on a skin-facing side of the substrate and arranged on the at least a portion of the microheating element such that it is configured to contact the user's skin and encircle an opening of the micropore; and
  an adhesive configured to be disposed on the skin-facing side of the substrate for adhering the patch to the skin of the user.

6. The device of claim 5, wherein the multiple antimicrobial materials are located in different portions of the generally ring shaped nanofiber mat.

7. The device of claim 6, wherein the different portions are individual sub-rings comprising the generally ring shaped mat.

8. The device of claim 6, wherein the different portions are alternating radial sections of the generally ring shaped mat.

* * * * *